(12) United States Patent
Hod et al.

(10) Patent No.: US 8,951,268 B2
(45) Date of Patent: Feb. 10, 2015

(54) SURGICAL FASTENING DEVICE WITH MESH RETAINING MEANS

(75) Inventors: Eitan Hod, Zichron Yaakov (IL); David Bleicher, Tel Aviv (IL); Boaz Manash, Givat-Ada (IL)

(73) Assignee: I.B.I. Israel Biomedical Innovations Ltd., Kibbutz Haogen (IL)

( * ) Notice: Subject to any disclaimer, the term of this patent is extended or adjusted under 35 U.S.C. 154(b) by 126 days.

(21) Appl. No.: 13/695,160

(22) PCT Filed: May 17, 2011

(86) PCT No.: PCT/IL2011/000388
§ 371 (c)(1), (2), (4) Date: Oct. 29, 2012

(87) PCT Pub. No.: WO2011/145091
PCT Pub. Date: Nov. 24, 2011

(65) Prior Publication Data
US 2013/0066339 A1    Mar. 14, 2013

Related U.S. Application Data

(60) Provisional application No. 61/345,335, filed on May 17, 2010.

(51) Int. Cl.
*A61B 17/10* (2006.01)
*A61B 17/068* (2006.01)
*A61B 17/00* (2006.01)
(Continued)

(52) U.S. Cl.
CPC ....... *A61B 17/0682* (2013.01); *A61B 17/00234* (2013.01); *A61B 17/068* (2013.01); *A61F 2/0063* (2013.01); *A61B 2017/00805* (2013.01); *A61B 2017/0641* (2013.01); *A61F 2002/0072* (2013.01)
USPC .......................................................... 606/139

(58) Field of Classification Search
USPC ......... 606/139, 142, 143, 151, 152, 153, 154, 606/155, 156, 157, 158, 228, 229, 230, 231, 606/232
See application file for complete search history.

(56) References Cited

U.S. PATENT DOCUMENTS 5,207,679 A * 5/1993 Li ................................ 606/232
5,354,292 A   10/1994 Braeuer et al.
(Continued)

FOREIGN PATENT DOCUMENTS

JP    2003515384    5/2003
WO   WO 95/30374    11/1995
(Continued)

OTHER PUBLICATIONS

International Search Report from International Application No. PCT/IL2011/000388 Mailed Oct. 7, 2011.

*Primary Examiner* — Ryan Severson
*Assistant Examiner* — Jonathan W Miles
(74) *Attorney, Agent, or Firm* — Dorsey & Whitney LLP

(57) ABSTRACT

The invention provides a surgical fastening or suturing device. The device of the invention has a slender shaft and an actuating mechanism configured to eject a surgical fastener from the distal end of the shaft or configured to perform suturing at the distal end of the shaft. The device also has an attachment arrangement for attaching a piece of surgical mesh material onto an external lateral surface of the shaft and around the distal end of the shaft.

5 Claims, 5 Drawing Sheets

(51) Int. Cl.
*A61F 2/00* (2006.01)
*A61B 17/064* (2006.01)

(56) References Cited

U.S. PATENT DOCUMENTS

| | | | |
|---|---|---|---|
| 5,370,650 A | 12/1994 | Tovey et al. | |
| 5,397,332 A | 3/1995 | Kammerer et al. | |
| 5,425,740 A | 6/1995 | Hutchinson, Jr. | |
| 5,478,353 A * | 12/1995 | Yoon | 606/213 |
| 5,522,845 A * | 6/1996 | Wenstrom, Jr. | 606/232 |
| 5,643,321 A * | 7/1997 | McDevitt | 606/232 |
| 5,649,963 A * | 7/1997 | McDevitt | 606/232 |
| 5,702,215 A * | 12/1997 | Li | 411/21 |
| 5,797,963 A * | 8/1998 | McDevitt | 606/232 |
| 5,814,005 A * | 9/1998 | Barra et al. | 604/8 |
| 5,814,071 A * | 9/1998 | McDevitt et al. | 606/232 |
| 5,817,113 A * | 10/1998 | Gifford et al. | 606/153 |
| 5,843,087 A * | 12/1998 | Jensen et al. | 606/104 |
| 5,843,127 A * | 12/1998 | Li | 606/232 |
| 5,849,004 A * | 12/1998 | Bramlet | 606/232 |
| 5,922,026 A | 7/1999 | Chin | |
| 6,620,176 B1 * | 9/2003 | Peterson et al. | 606/153 |
| 8,162,942 B2 * | 4/2012 | Coati et al. | 606/63 |
| 8,409,252 B2 * | 4/2013 | Lombardo et al. | 606/232 |
| 2004/0199189 A1 * | 10/2004 | Gifford et al. | 606/155 |
| 2007/0088390 A1 | 4/2007 | Paz et al. | |
| 2009/0125041 A1 | 5/2009 | Dudai | |
| 2009/0281563 A1 | 11/2009 | Newell et al. | |
| 2010/0114126 A1 | 5/2010 | Neff | |

FOREIGN PATENT DOCUMENTS

| | | |
|---|---|---|
| WO | WO 01/39694 | 6/2001 |
| WO | WO 2009/022348 | 2/2009 |

* cited by examiner

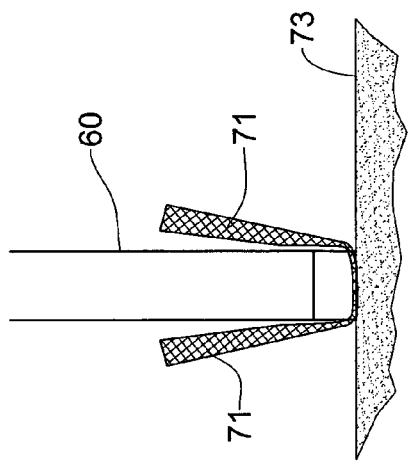
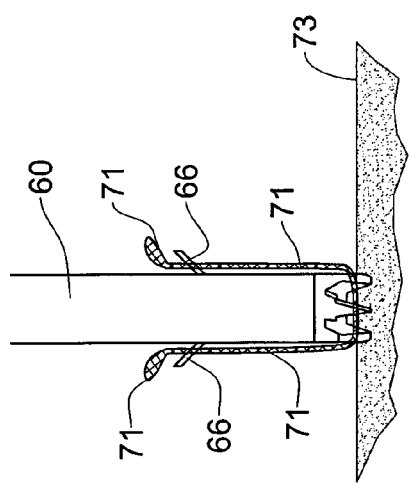
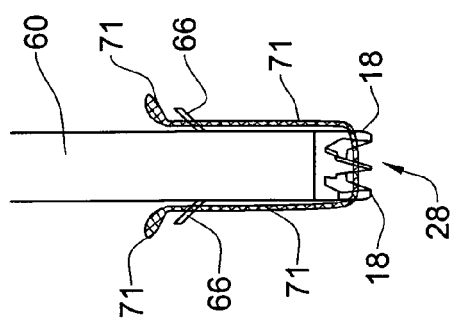
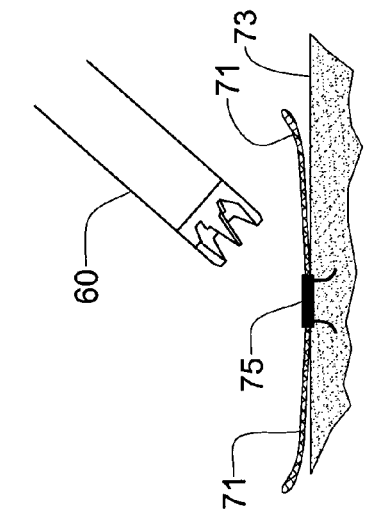
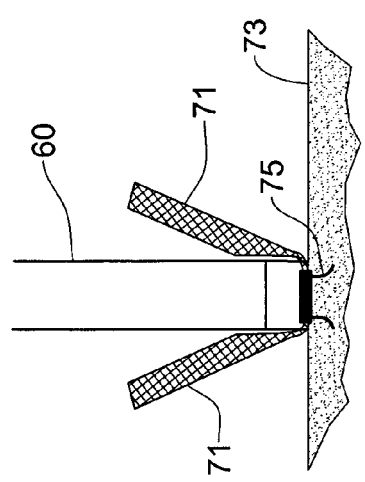

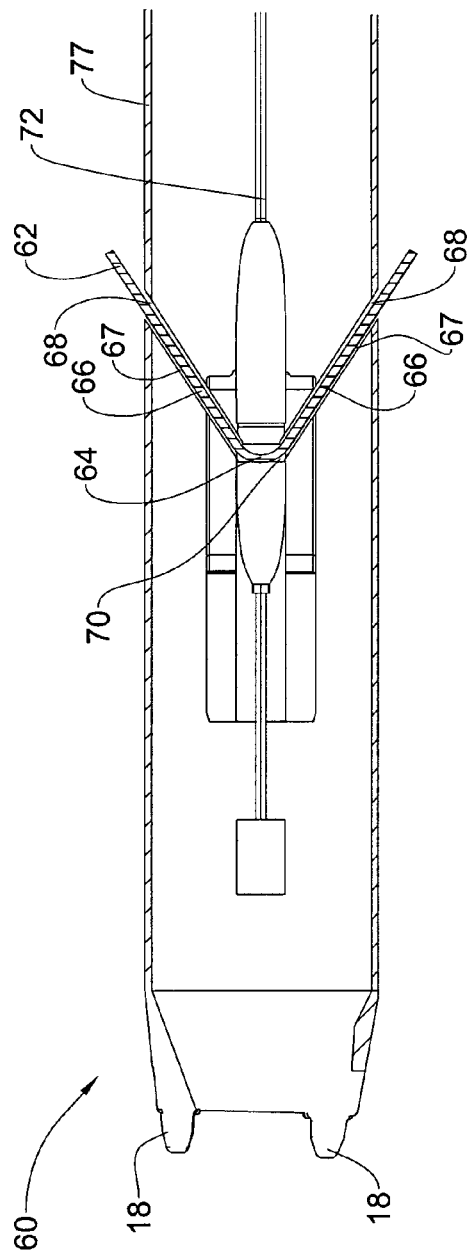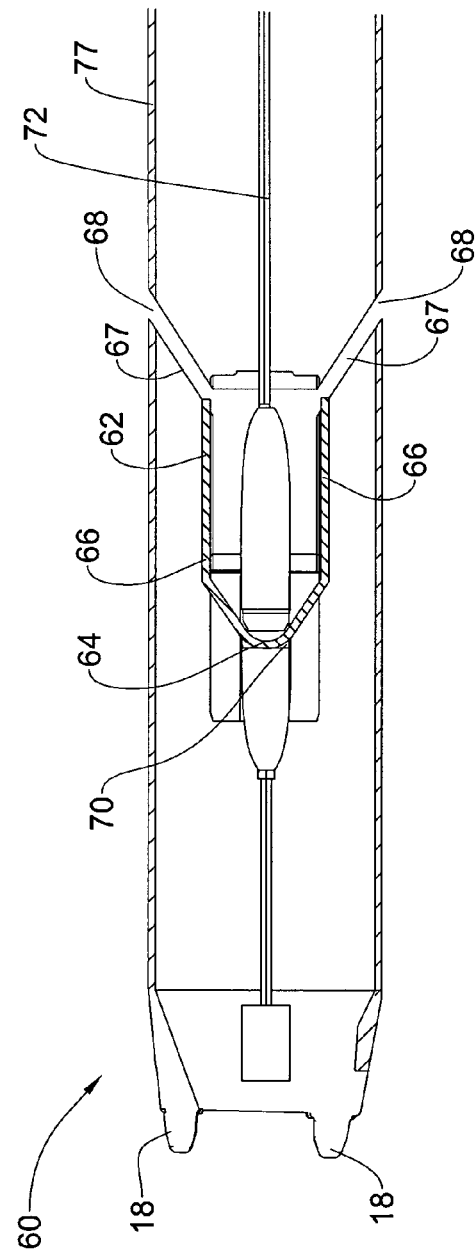

SURGICAL FASTENING DEVICE WITH MESH RETAINING MEANS

FIELD OF THE INVENTION

This invention relates to surgical devices, and more particularly to such devices for surgical fastening or suturing.

BACKGROUND OF THE INVENTION

Surgical mesh material has several uses in surgery, such as positioning and immobilizing body organs or to support a body organ. Typically, the mesh is attached to body tissues at two or more locations by suturing or using surgical fasteners. For example, in inguinal hernia surgery, a polypropylene mesh is fastened to the abdominal wall in order to reinforce the abdominal wall. Insertion of mesh has also been used in the treatment of uterine prolapse, hernia, and urinary incontinence.

A variety of suturing devices as well as fastening devices are available for endoscopic or open procedures, to attach a strip or patch of mesh to a tissue. Many of these devices have a handle portion from which slender shaft extends that can be introduced into a body cavity with a small incision. At the distal end of the shaft are means for suturing or deploying a surgical fastener in a body tissue surface inside the cavity. In most of the surgical fastening devices, the shaft stores one or more surgical fasteners. An actuating mechanism contained in the handle portion ejects one or more fasteners from the distal end of the shaft. If the body tissue is accessible from two opposite sides, a fastening device may be used having an anvil that deforms the prongs of fastener after having passed through the body tissue. When the tissue is not accessible from two opposite sides, a fastening device not having an anvil is used. In one such fastening device, a fastener is screwed into the tissue. In another fastening device, disclosed in WO2009/022348, a fastener is used having a crown from which extend two or more prongs. The prong tips are retained in a baseplate. The fastener is deployed using a fastening device that moves the crown towards the baseplate. As the crown approaches the baseplate, the prongs splay radially outward as they penetrate the tissue.

In many applications, the surgeon manipulates the mesh into the desired position in the body using one hand, and then operates the suturing or fastening device with the other hand in order to affix the mesh to tissue surfaces. Manipulating the mesh and the fastening device in this way can be awkward. Thus, fastening devices are known in which a piece of mesh is retained on the tip of the shaft so that as a fastener is deployed the prongs pass through the mesh before entering the tissue.

For example, WO2009/022348 discloses providing the distal end of the shaft with one or more projections configured to engage a surgical mesh material and retain the mesh over the tip of the shaft. A piece of a surgical mesh material is engaged onto the projections at a first region of the mesh material. The distal end of the shaft with the surgical mesh material engaged on its tip is then delivered to a first location on a tissue surface. The actuating mechanism of the device is then actuated to eject a fastener from the distal end of the shaft into the tissue at the first location. As the fastener is ejected from the distal end of the shaft, the prongs of the fastener pass through the mesh so as to pin the mesh to the tissue at the first location.

SUMMARY OF THE INVENTION

The present invention provides a surgical fastening or suturing device for attaching a piece of mesh to a tissue surface. The device of the invention has a slender shaft extending from a handle portion. The handle portion includes an actuating mechanism whose activation results in suturing or fastening at the distal end of the shaft. In accordance with the invention, the fastening device is provided with attachment means for attaching a piece of mesh to one or more locations on the external lateral surface of the shaft. A piece of mesh is mounted on the attachment means with the mesh covering the shaft tip. The shaft tip is then applied to a body tissue surface and the actuating mechanism is activated. In the case of surgical fastening device, the deployed fastener passes through the mesh before becoming embedded in the body tissue, pinning the mesh to the tissue surface. In the case of a suturing device, the mesh becomes sutured to the tissue surface. Either during or after deployment of the fastener or the suturing, the mesh is released from the attachment means. In some embodiments, the mesh is released from the attachment means by manual manipulation of the shaft. In other embodiments, the device is provided with releasing means for releasing of the mesh from the attachment means. In one embodiment, the releasing means is activated by the actuating mechanism in order to release the mesh from the lateral surface of the shaft just before it is affixed to the tissue.

In one embodiment, the attachment means comprises two or more hooks that extend radially outward from the lateral surface of the shaft. A releasing mechanism may be provided which automatically retracts the hooks into the interior of the shaft just before the mesh is affixed to the tissue surface. In another embodiment, the attachment means comprises one or more C-shaped clips that clip onto the shaft over the mesh. After attachment of the mesh, the clips are manually detached from the shaft. The clips may be detached by means of one or more cords or handles extending from the clips to the proximal end of the device where it accessible to the user.

In another embodiment, the attachment means comprises a sleeve that is placed around the shaft and surrounding a section of the mesh to maintain the mesh on the lateral surface of the shaft. After suturing or fastening, the sleeve is removed from around the shaft. Removal of the sleeve may be accomplished by tearing the sleeve, and this may be facilitated by preformed perforations in the sleeve material. Tearing of the sleeve may be performed by pulling on a cord extending from the sleeve to the handle portion of the device.

The surgical device of the invention may be used with any type of deployment mechanism.

The invention thus provides a surgical fastening or suturing device comprising:
  (a) a slender shaft having a proximal end and a distal end;
  (b) an attachment arrangement configured to attach a piece of surgical mesh material onto an external lateral surface of the shaft and around the distal end of the shaft; and
  (c) an actuating mechanism configured to eject a surgical fastener from the distal end of the shaft or configured to perform suturing at the distal end of the shaft.

The device of the invention may further comprise a releasing mechanism releasing the mesh from the lateral surface of the shaft.

The releasing mechanism may release the mesh prior to or during ejecting a fastener or prior to suturing. The releasing mechanism may release the mesh after ejecting a fastener or after suturing. The actuating mechanism may activate the releasing mechanism.

The attachment arrangement may comprise one or more hooks on the lateral surface of the shaft. When the attachment arrangement comprises one or more hooks on the lateral surface of the shaft, the releasing mechanism may retract the hooks into an interior of the shaft.

The attachment arrangement may comprise a clip adapted to clamp onto the shaft. When the attachment arrangement comprises a clip adapted to clamp onto the shaft, the releasing mechanism may comprises a handle or cord configured to remove the clip from the shaft. The handle may be provided with a stopper.

The attachment arrangement may comprise a sleeve dimensioned to fit onto the shaft. When the attachment arrangement comprises a sleeve dimensioned to fit onto the shaft, the detachment mechanism may tear the sleeve. In this case, the sleeve may be provided with perforations to facilitate tearing of the sleeve. The detachment means may further comprise a cord extending from the sleeve to the proximal end of the device, the sleeve tearing when the cord is pulled.

The attachment arrangement may comprise knobs extending from the lateral surface of the shaft.

The device of the invention may further comprise one or more protrusions extending distally from the distal end of the shaft.

BRIEF DESCRIPTION OF THE DRAWINGS

In order to understand the invention and to see how it may be carried out in practice, embodiments will now be described, by way of non-limiting example only, with reference to the accompanying drawings, in which:

FIGS. 3a to 3e show use of the surgical fastening device of FIG. 4 to attach a mesh material to a tissue surface;

FIG. 4 shows a surgical fastening device in accordance with one embodiment of the invention comprising retractable hooks for retaining mesh, before retraction of the hooks (FIG. 4a) and after retraction of the hooks (FIG. 4b)

DETAILED DESCRIPTION OF EMBODIMENTS

The invention will now be described in reference to a surgical fastening device, it being evident from the description how the invention can be implemented in a surgical suturing device.

Figure 1:
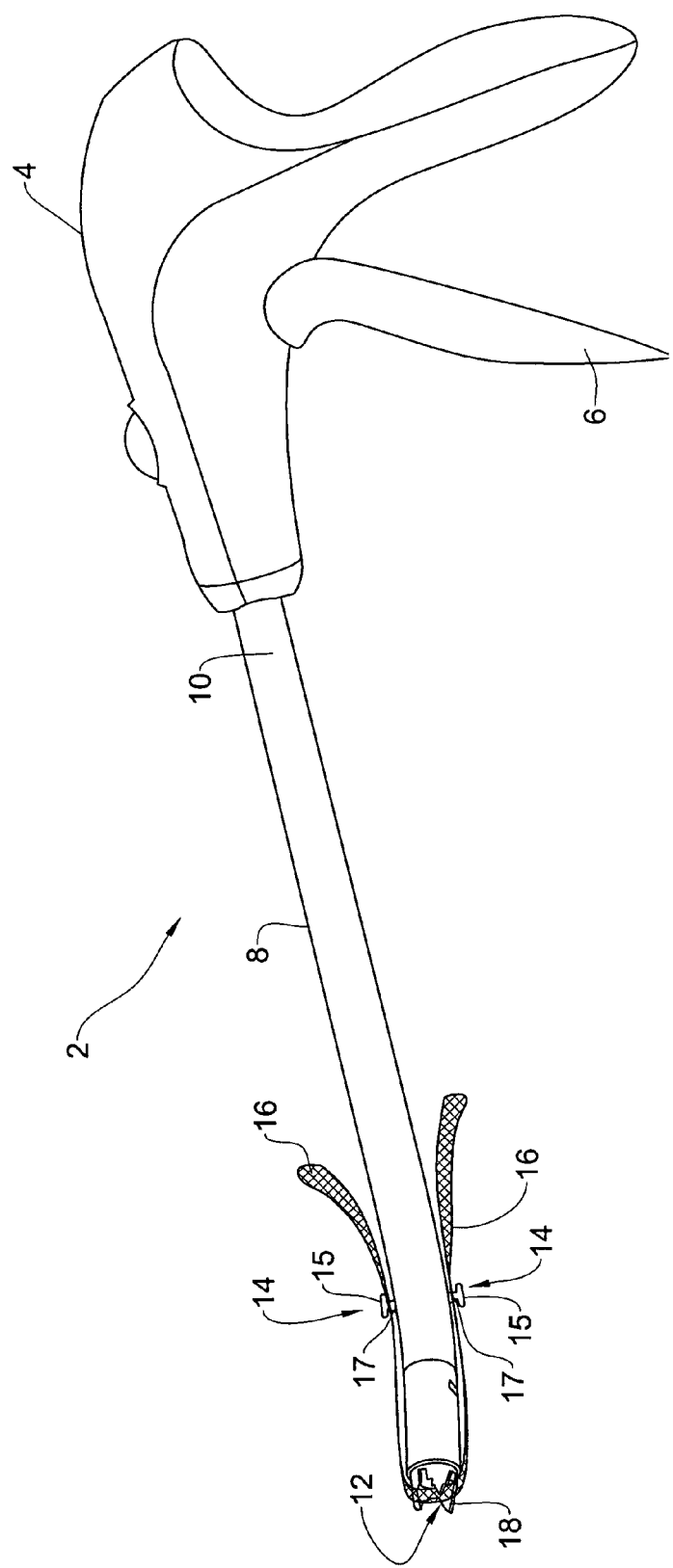
FIG. 1 shows a surgical fastening device in accordance with one embodiment of the invention comprising knobs for retaining mesh.

FIG. 1 shows a device 2 for deploying one or more surgical fasteners in accordance with one embodiment of the invention. The device 2 has a handle portion 4 containing an actuating mechanism including an actuating lever 6. A hollow slender shaft 8 extends from the handle portion 4 and stores one or more surgical fasteners. The shaft 8 has a proximal end 10 attached to the handle portion 4 and a distal end 12. Depressing the actuating lever 6 causes a surgical fastener inside the shaft 8 (not seen in FIG. 1) to be ejected from the distal end 12 of the shaft.

In accordance with the invention, the device 2 is provided with attachment means for attaching a piece of mesh to the distal end of the shaft. In this embodiment, the attachment means includes two or more knobs 14 extending radially outward from the external lateral surface of the shaft near the distal end of the shaft. The knobs may terminate in a bulb 15 that is separated from the shaft surface by a stem 17. This arrangement allows the knobs to retain a piece of mesh 16 on the shaft, with the mesh covering the distal end of the shaft 12. The distal end 12 of the shaft may be provided with distally facing projections 18 that are designed to retain the mesh 16 at the distal end of the shaft and thus prevent the mesh from slipping off the tip. As a fastener (not shown in FIG. 1) is ejected from the distal end of the shaft, prongs of the fastener pass through the mesh 16 before becoming embedded in a body tissue to pin the mesh to the body tissue. After pinning the mesh to the body tissue, the mesh can be released from the knobs 14.

FIG. 4a shows the distal end of a shaft 77 of a surgical fastening device 60 in accordance with another embodiment of the invention. The fastening device 60 has several features in common with the device 2 shown in FIG. 1, and common elements are indicated by the same reference numeral in both embodiments, without further comment. The device 60 has a wire 62 that is initially "V" shaped having a vertex 64 and two arms 66. As shown in FIG. 4a, the arms 66 lie in channels 67 in the interior of the shaft 77 and extend through a pair of diametrically opposed apertures 68 in the wall of the shaft 77. When extending through the apertures 68, as shown in FIG. 4a, the arms serve to attach a piece of mesh 71 to the lateral surface of the shaft, as explained below. The vertex 64 is immobilized in a groove 70 in an actuating rod 72 of the actuating mechanism of the device 60. Displacement of the actuating rod towards the distal end of the shaft (FIG. 4b) causes a surgical fastener (not shown) to be ejected from the distal end of the shaft and simultaneously displaces the vertex distally inside the shaft. As the vertex moves distally, the arms 66 are retracted through the apertures 68 into the interior of the shaft to release the mesh from the lateral surface of the shaft just prior to ejection of the fastener.

Figure 2A:
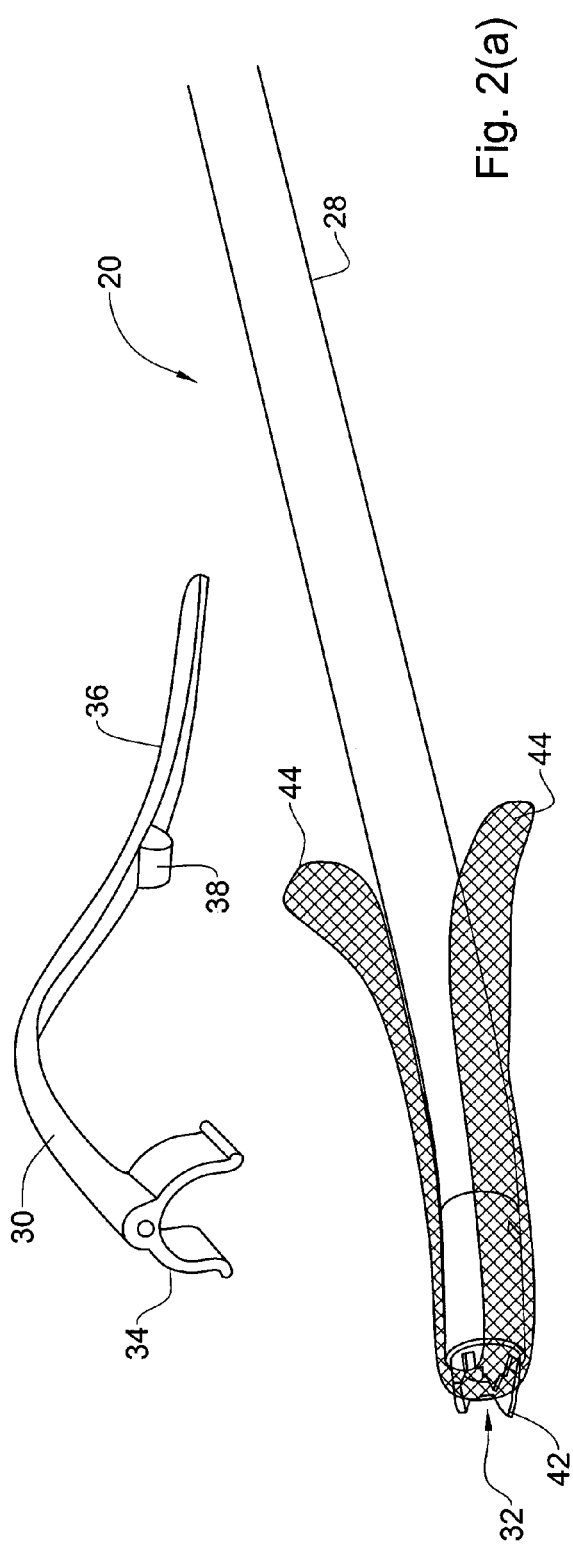
FIG. 2 shows a surgical fastening device in accordance with another embodiment of the invention comprising a clip for retaining mesh retaining, before attachment of the clip (FIG. 2a) and after attachment of the clip (FIG. 2b)

FIG. 2a shows the distal end of the shaft 28 of a device 20 for deploying one or more surgical fasteners in accordance with another embodiment of the invention. The device 20 has an actuating mechanism not shown in FIG. 2a for ejecting a surgical fastener from the distal end 32 of the shaft as explained above with reference to the device 2 shown in FIG. 1.

Figure 2B:
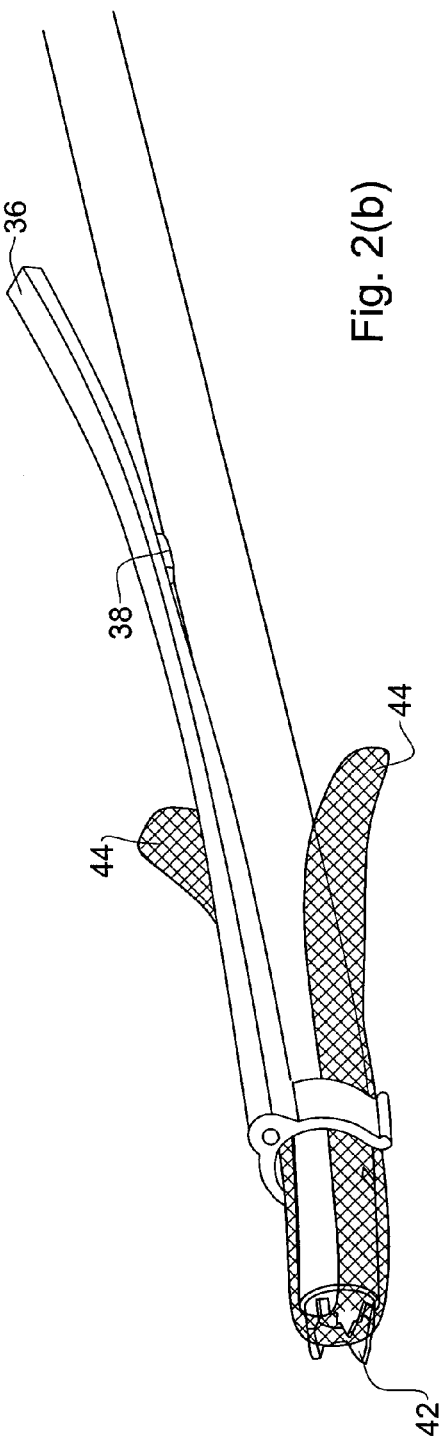

The device 20 is provided with attachment means for attaching a piece of mesh 44 to the distal end of the shaft. In this embodiment, the attachment means includes a clip 30. The clip 30 has a partial cylindrical surface 34 attached to a curved handle 36. After positioning a piece of mesh 44 around the distal end 32 of the shaft 28, as shown in FIG. 2a, the clip is made to snap onto the shaft 28 over the mesh as shown in FIG. 2b. As with the device 2 of FIG. 1, the distal end 32 of the shaft 28 may be provided with distally facing projections 42 that are designed to grasp the mesh 44 at the distal end of the shaft. As a fastener (not shown in FIG. 2) is ejected from the distal end of the shaft, prongs of the fastener pass through the mesh 44 before becoming embedded in a body tissue to pin the mesh to the body tissue. After pinning the mesh to the body tissue, the clip 34 can be removed from the shaft by depressing the curved handle 36 towards the shaft, or by pulling the handle away from the shaft, to release the mesh from around the shaft. A knob 38 on the handle 36 may serve as a pivot for rotation of the clip 30 or as a stopper preventing inadvertent release of the clip. In another embodiment (not shown), the clip is removed by means of a cord, instead of the handle 36, extending from the cylindrical surface 34 to the actuating mechanism.

Figure 5:
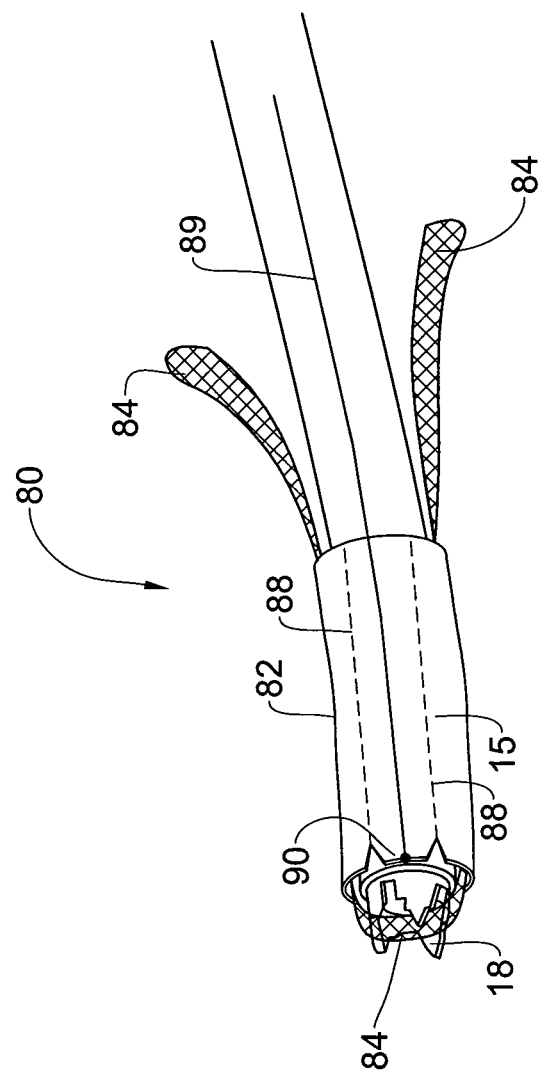
FIG. 5 shows a surgical fastening device in accordance with an embodiment of the invention comprising a tearable sleeve.

FIG. 5 shows the distal end of a shaft 80 of a surgical fastening device in accordance with yet another embodiment of the invention. The fastening device 80 has several features in common with the device 2 shown in FIG. 1, and common elements are indicated by the same reference numeral in both embodiments, without further comment. The device 80 is provided with a sleeve 82 that is dimensioned to slide over the shaft 80 after mounting a piece of mesh 84 around the distal end of the shaft 18. After surgical fastening or suturing, the sleeve is removed from the shaft by tearing the shaft by pulling on a cord 89 attached to a tab 90 on the sleeve and extending from the sleeve to the proximal end of the device 80. Tearing of the sleeve is facilitated by two longitudinal rows of preformed perforations 88 in the sleeve.

FIG. 3 shows schematically a surgical procedure using the device 60 of FIG. 4. In FIG. 3*a*, a piece of mesh 71 is mounted on the prongs 18 and on the arms 66 of the "V" shaped wire 62 The distal end of the shaft 28 with the mounted mesh 71 is applied to a tissue surface 73 to which the mesh is to be affixed (FIG. 3*b*). The actuating mechanism is then activated. This causes the arms 66 to be retracted into the shaft, as explained above, and thus release of the mesh 71 from the lateral surface of the shaft (FIG. 3*c*). During release of the mesh from the lateral surface of the shaft, a surgical fastener 75 is ejected from the distal end of the shaft to pin the mesh to the tissue surface (FIG. 3*d*). The prongs 18 can then be disengaged from the mesh. The procedure may be repeated as required to fasten the mesh to tissue surfaces with as many fasteners as is desired.

The invention claimed is:

1. A surgical fastener or suturing device comprising:
   (a) a slender shaft having a proximal end and a distal end;
   (b) a surgical mesh material;
   (c) an attachment arrangement configured to attach the surgical mesh material onto an external lateral surface of the shaft and around the distal end of the shaft, the attachment arrangement including one or more hooks on the lateral surface of the shaft;
   (d) an actuating mechanism configured to eject a surgical fastener from the distal end of the shaft or configured to perform suturing at the distal end of the shaft; and
   (e) a releasing mechanism configured to release the surgical mesh material from the lateral surface of the shaft by retracting the hooks into an interior of the shaft.

2. The device according to claim 1 wherein the releasing mechanism releases the surgical mesh material prior to or during ejecting a fastener or prior to suturing.

3. The device according to claim 1 wherein the releasing mechanism releases the surgical mesh material after ejecting a fastener or prior to suturing.

4. The device according to claim 1 wherein the actuating mechanism activates the releasing mechanism.

5. The device according to claim 1 further comprising one or more protrusions extending distally from the distal end of the shaft.

\* \* \* \* \*